United States Patent [19]

Dotson et al.

[11] 4,414,974
[45] Nov. 15, 1983

[54] MICROSURGICAL KNIFE

[75] Inventors: Robert S. Dotson, Manhattan, Kans.; W. George Richeson, Marietta, Ga.; Herb M. Trenka, Clearwater, Fla.

[73] Assignee: General Conveyors Limited, Stamford, United Kingdom

[21] Appl. No.: 271,967

[22] Filed: Jun. 9, 1981

[51] Int. Cl.³ ............................................. A61B 17/32
[52] U.S. Cl. .................................... 128/305; 30/162; 30/295
[58] Field of Search ............... 128/305, 751, 314, 315, 128/329 R, 329 A, 339; 30/151, 293, 286, 294, 295, 162, 163; 433/116

[56] References Cited

U.S. PATENT DOCUMENTS

| | | | |
|---|---|---|---|
| 868,393 | 10/1907 | Ames | 30/151 |
| 1,356,799 | 10/1920 | Tompson | 30/332 |
| 1,548,139 | 8/1925 | Grimm | 30/332 |
| 2,390,309 | 12/1945 | Keys | 30/293 |
| 2,512,237 | 6/1950 | Mravik | 30/151 |
| 3,001,522 | 9/1961 | Silverman | 128/305 |
| 3,039,468 | 6/1962 | Price | 128/329 |
| 3,688,773 | 9/1972 | Weiss | 128/329 X |
| 3,840,015 | 10/1974 | Gain | 128/339 X |
| 3,905,375 | 9/1975 | Toyama | 128/329 A |

Primary Examiner—Michael H. Thaler
Attorney, Agent, or Firm—Sandler & Greenblum

[57] ABSTRACT

A disposable, or one-time-use microsurgical knife has a slidable shroud that can be moved into a forward position to protect the blade, and can be moved rearwardly to allow use of the knife. The shroud, as well as other parts of the knife, are made of plastic, and a phosphorescent material is included to render the knife luminescent during steps taken in a darkened operating room. The extremely sharp razor chip blade includes a shank selectively wedged into the knife body so blades are interchangeable.

7 Claims, 5 Drawing Figures

U.S. Patent    Nov. 15, 1983    4,414,974
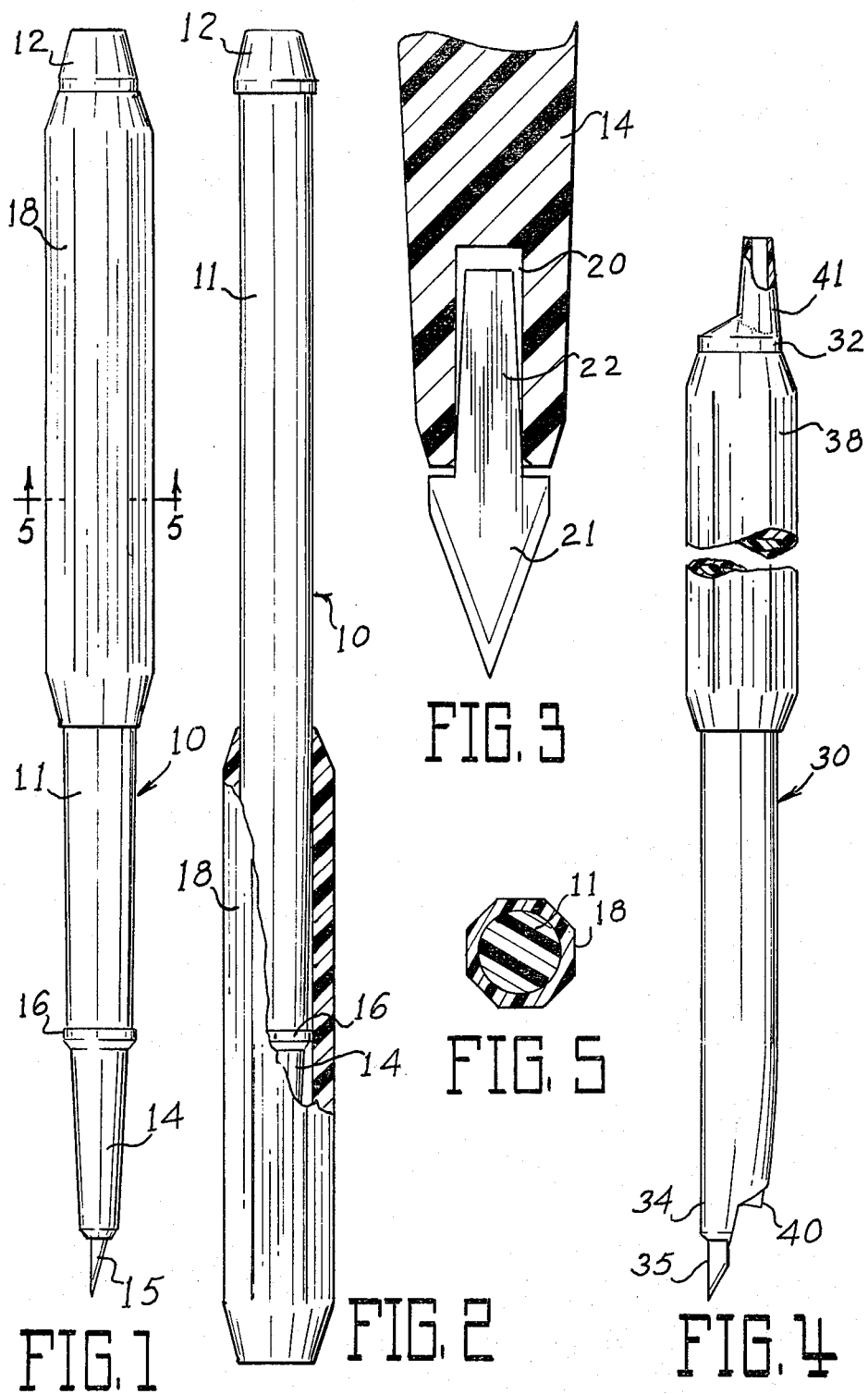

MICROSURGICAL KNIFE

FIELD OF THE INVENTION

This invention relates generally to microsurgical implements, and is more particularly concerned with a disposable microsurgical knife having a selectively useable blade guard.

BACKGROUND OF THE INVENTION

It has become almost commonplace for surgeons to perform operations on very delicate organs of the body such as the eye or ear, this surgery frequently being performed under a microscope, and certainly dealing with microscopic dimensions. The area of surgery has become known as microsurgery, and there is a variety of instruments for use in performing microsurgery. One instrument is a type of extremely sharp cutting implement that utilizes a disposable razor chip. The extreme sharpness of the blades makes them highly desirable in microsurgery, but also renders them very hazardous in passing the knives back and forth between the surgeon and the operating assistant. This is especially true in modern ophthalmic surgery in which the operating room is frequently darkened. Sometimes there is simply a low level of lighting, and at other times all lights are extinguished except for illumination provided by the operating microscope of the surgeon. It will be appreciated that the extremely sharp knives can very easily cut a glove, and the skin beneath the glove; and, if the knife has already been used on a patient, there is an obvious danger of infection. Another difficulty with the extremely sharp razor knives is that the blades are very easy to ruin so that if the sharp edge of the knife contacts another instrument, an instrument tray, or other reasonably hard substance, the knife blade can be completely ruined. It must be kept in mind that the surgery involved is operating in the range of tenths of a millimeter, with suture material measured in microns. Thus, a usually unnoticeable burr on the knife blade would render the knife damaged beyond use in this environment.

Since the advent of the disposable, extremely sharp knives, various packaging means have been devised in order to allow the knives to be shipped and stored without damage to the blade. Obviously, the packaging must be sturdy, and is frequently quite involved to be sure that nothing touches the sharp edge of the blade. As a result, while the knife may be successfully shipped to the point of use, and stored until the time of use, the blade may be damaged during its removal from the packaging. Also, once the blade is removed from the packaging, there is no longer any protection for the blade and the blade may be easily damaged, or cause damage, in the operating room itself. This is most especially true in ophthalmic surgery when the operating room is dark, or has a very low level of lighting so that the surgical assistant may be working with memory and feel more than with eyes.

SUMMARY OF THE INVENTION

The present invention overcomes the above mentioned and other difficulties with the prior art microsurgical disposable knives by providing a generally elongate knife body having a slidable shroud disposed around the body. The shroud is slidable between one extreme position in which the shroud is supported by the knife body and surrounds the blade which is carried by one end of the knife body, and to an opposite extreme position at the opposite end of the knife body. The shroud is disposable at any selected position along the knife body between these two extremes, so the surgeon can hold the knife in whatever manner is most effective and efficient for the particular surgeon; however, before the surgeon hands the knife to an assistant, the shroud can be slipped back over the knife blade so the knife is rendered safe. Further, it is contemplated that the moveable shroud and/or other portions of the knife of the present invention will be molded of a plastic material, and a phosphorescent material will be included in the plastic, thereby rendering the knife luminescent for easy location during an operation in a darkened operating room. Furthermore, the knife of the present invention includes a selectively removable blade to allow a single knife body to be used for various steps during the procedure, or to allow replacement of a damaged blade during a procedure. In one embodiment of the invention, it is contemplated that the knife will be provided with a source of "cold light" which may be used if desired.

BRIEF DESCRIPTION OF THE DRAWINGS

These and other features and advantages of the present invention will become apparent from consideration of the following specification when taken in conjunction with the accompanying drawings in which:

FIG. 1 is a side elevational view of a microsurgical knife made in accordance with the present invention, the shroud being shown in its extreme rearward position;

FIG. 2 is a side elevational view, partially in cross-section, showing the knife of FIG. 1 with the shroud moved into blade-protecting position;

FIG. 3 is an enlarged, fragmentary cross-sectional view showing the mounting means for the knife blade;

FIG. 4 is a side elevational view, partially broken away, showing a modified form of the knife of the present invention; and, FIG. 5 is a cross-sectional view taken on the line 5—5 in FIG. 1.

DESCRIPTION OF THE PREFERRED EMBODIMENTS OF THE INVENTION

Referring now more particularly to the drawings, and to those embodiments of the invention here chosen by way of illustration, it will be seen in FIGS. 1 and 2 that the knife body generally designated at 10 includes a generally cylindrical portion 11 having an enlarged cap 12 at the rearmost end thereof.

The forward end of the knife body 10 has a frustoconical section 14 that is smaller in diameter than the cylindrical portion 11. The knife body 10 therefore provides a smaller forward tip 14 to allow the surgeon a better view of the cutting blade 15 and the operating site. Between the forward frustoconical section 14 and the cylindrical body 11, there is a transition member 16 which has an outside diameter slightly larger than the cylindrical portion 11 of the knife body 10.

Looking now particularly at FIG. 2 of the drawings, it will be understood that the cylindrical portion 11 is not of uniform diameter throughout its length; rather, the diameter of the cylindrical portion 11 is somewhat reduced adjacent to the transition member 16, and is slightly enlarged in the direction of the rearward cap 12. The reduction of the diameter of the member 11 adjacent to the transition member 16 provides a more comfortable grip for the surgeon since it is natural to have an instrument reduced in diameter towards the forward end. The increase in diameter of the cylindrical member 11 may be very slight, perhaps a few hundredths of a millimeter, but this is sufficient for the shroud 18 to be somewhat wedged in its rearmost position as shown in FIG. 1 of the drawings. It will be understood that the shroud 18 will not be so tightly wedged onto the member 11 that it is extremely difficult to remove; rather, the fit is sufficiently close that the shroud 18 will become reasonably tight and require a definite effort to move the shroud forward.

When the shroud 18 is moved forward, it will be understood that the object is to protect the blade 15, so the shroud 18 cannot be allowed to move radially to a significant extent with respect to the knife body 10. The transition member 16 acts as a spacing washer to prevent such motion. It will be understood that the diameter of the transition member 16 is approximately equal to the diameter of the member 11 generally in the center thereof.

It is contemplated that the entire knife body 10 will be molded of plastic, and of course the shroud 18 will be molded of plastic and the two subsequently assembled. Thus, it will be understood that the entire knife body 10 and the shroud 18 may be molded of a plastic that includes a phosphorescent material so the entire knife will be visible in the dark. Alternatively, however, the shroud 18 may be molded of phosphorescent plastic and the knife body 10 molded of ordinary, non-phosphorescent, plastic. It is of course a matter of choice as to whether the entire knife body 10 and the shroud 18 would be molded of phosphorescent plastic, or having only the shroud 18 in phosphorescent plastic would reduce the cost, and this would provide sufficient visibility for the operating room personnel to locate the knife when needed.

Those skilled in the art will realize that different knife blades are frequently used in one surgical procedure. There are several standard sizes of blades such as that shown in FIG. 3 of the drawing whereby the surgeon can insert the knife blade straight forward through tissue to provide a predetermined length of cut. It is frequently necessary to provide two or more incisions of different lengths, and some surgeons prefer to use blades such as that shown in FIG. 3 to provide precisely the correct length of incision. For other steps during the same procedure, the blade such as that shown in FIG. 1 or FIG. 4 may be required.

The knife of the present invention includes a slot 20 in the forward frustoconical portion 14 of the knife body 10 for receipt of the knife blade 21. It will be understood that the various blades for use in the knife of the present invention would have shanks identically made while only the cutting tips would vary. Thus, the shank 22 of the knife blade is formed with tapering sides which will cause the shank 22 to wedge within the slot 20, since the slot 20 has straight sides. The taper on the shank 22 should be sufficient to provide an easy lock, but be releasable with effort. A taper amounting to a difference of 2 or 3 tenths of a millimeter over a shank length of around 4 to 6 millimeters works quite well, though of course these dimensions may be varied considerably depending on the particular results desired. FIG. 3 has the taper exaggerated for purposes of illustration.

Looking now at FIG. 4 of the drawings, it will be understood that the knife body 30 is generally like the knife body 10 previously described, having a rear cap 32 and a moveable shroud 38. It will be seen in FIG. 4 of the drawings that the forward end of the body 30, designated at 34, is offset, but contains a slot as previously described in order to receive the knife blade 35. At the tip 34, there is a cylindrical member 40 which extends throughout the length of the body 30 and terminates in a male fitting 41 projecting from the rear of the cap 32. The member 40 is a plastic fiber, or group of fibers, constituting a light pipe. The fitting 41 is contemplated to be a conventional device to receive existing sources of light so that the present instrument can be connected to conventional "cold light" sources. The light is conducted from the fitting 41, through the body 30, and is emitted at the member 40. It will be observed that the member 40 is adjacent to the knife blade 35, and is disposed on the sharpened side of the blade 35. As a result, the surgeon can see clearly in the direction of the cut. It will also be obvious that the light source can be easily disconnected from the member 41, and the knife shown in FIG. 4 of the drawings can be used the same as the knife shown in FIGS. 1 and 2 of the drawings.

It will therefore be seen from the foregoing discussion that the present invention provides a microsurgical knife that is sufficiently inexpensive to be disposable, which is to say a one-time-use knife. Even though the knife is disposable, the knife body can be provided with one of selected blades, and the changeable blades can be used to provide for different steps during a single procedure, or to replace a damaged blade. The shroud 18 can be disposed over the blade as shown in FIG. 2 of the drawings, and the packaging for the knife can be very simple and inexpensive since the shroud 18 protects the knife blade 15 both from cutting the package and from damage to the blade. When the knife is opened and removed from the packaging, the shroud 18 can remain in place protecting the blade 15 until the knife is handed to the surgeon. The surgeon can then move the shroud 18 rearwardly to the extent desired; and, before the surgeon hands the knife to an assistant, the shroud 18 can be slipped back over the blade 15 to protect both the blade and the personnel in the operating room.

With at least the shroud 18 made of phosphorescent plastic material, it will be understood that the knife will absorb light in the initial setup period in the operating room; then, when the lights are lowered or extinguished for the operation, or for certain steps during the operation, the phosphorescent material will render the knife sufficiently luminescent for easy location in the dark, and for maximum safety.

As is clearly shown in FIG. 5 of the drawings, the shroud 18 is non-circular in cross-section. The shroud 18 is here shown as shaped as a regular octagon in cross-section; and, this particular shape is selected to give the knife a proper "feel" to the surgeon. The regular shape allows the surgeon to have a tactile sensation of rotation of the knife during use in addition to the visual inspection. Most importantly, however, the non-circular cross-section is desirable so the knife will not roll when placed on a tray, or otherwise move inadvertently. Thus, while the octagonal shape is shown, a hexagonal or other non-circular shape will also achieve the desired function.

It will of course be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as defined in the appended claims.

We claim:

1. A disposable microsurgical knife comprising an elongate knife body having a forward end and a rearward end, a cutting blade carried at said forward end and extending therefrom, and a shroud slidably received over said knife body, said shroud being selectively slidable towards and rearward end for exposing said cutting blade and providing a blade using position and slidable over said forward end for covering said cutting blade and providing a blade protecting position, said forward end of said knife body defining a slot therein, said slot having generally parallel side walls, said cutting blade including a cutting portion and a shank carrying said cutting portion, said shank having non-parallel edges, said shank being dimensioned to be received within said blade receiving slot to be locked therein by means of said non-parallel edges with said cutting portion extending from said shank beyond said knife body, said forward end of said knife body having a reduced diameter for allowing better visibility of said cutting blade, said rearward end of said knife body being a generally cylindrical portion and carrying an enlarged cap at the rearmost end thereof, said shroud having a non-circular exterior configuration and defining a circular bore therethrough, said generally cylindrical portion having an external diameter sized to cause said shroud to wedge in place when said shroud is slid to said blade using position, said knife body including means for centering said shroud when said shroud is slid to said blade protecting position, said shroud having a length sufficient to be supported by said cylindrical portion of said knife body and to extend beyond said cutting portion of said blade.

2. A microsurgical knife as claimed in claim 1, said knife body and said shroud being formed of a plastic material, at least a portion of said plastic material including a phosphorescent material therein.

3. A microsurgical knife as claimed in claim 2, wherein said shroud is formed of plastic material having phosphorescent material therein.

4. A microsurgical knife as claimed in claim 1, and further including a light pipe extending through said knife body, a connector formed integrally with said cap and extending from said rearward end of said knife body and in light transmitting communication with said light pipe, said light pipe projecting from said knife body adjacent to said cutting blade.

5. A microsurgical knife as claimed in claim 4, said blade being off-set from the axial centerline of said knife body in a first radial direction, said light pipe being off-set from said centerline in the opposite radial direction, said cylindrical portion of said knife body extending forward sufficiently to constitute said means for centering said shroud.

6. A microsurgical knife as claimed in claim 1, said forward end of said knife body defining a frustoconical section, said reduced diameter at said forward end being the smaller diameter of said frustoconical section, and a spacer between said cylindrical portion and said frustoconical section, said spacer having a diameter approximately equal to the diameter of said cylindrical section immediately adjacent to said cap, so that said spacer constitutes said means for centering said shroud.

7. A microsurgical knife as claimed in claim 6, said cap having a diameter larger than said circular bore through said shroud so that said cap acts as a rearward stop for said shroud.

* * * * *

UNITED STATES PATENT AND TRADEMARK OFFICE
CERTIFICATE OF CORRECTION

PATENT NO. : 4,414,974
DATED : November 15, 1983
INVENTOR(S) : Robert S. Dotson, W. George Richeson & Herb M. Trenka It is certified that error appears in the above-identified patent and that said Letters Patent are hereby corrected as shown below:

On the title page,

The Assignee should be deleted, the patent being unassigned.

The name of the Attorney should read: James B. Middleton.

Claim 1, line 11, change "towards and rearward end" to ---towards said rearward end---.

Signed and Sealed this

Nineteenth Day of June 1984

[SEAL]

Attest:

Attesting Officer

GERALD J. MOSSINGHOFF
Commissioner of Patents and Trademarks